United States Patent
Wong et al.

[11] Patent Number: 6,117,661
[45] Date of Patent: Sep. 12, 2000

[54] MUTANT MONO-OXYGENASE CYTOCHROME P450CAM

[75] Inventors: Luet-Lok Wong, Oxford; Sabine Lahja Flitsch, Edinburgh; Darren Paul Nickerson, Oxford; Alwyn James Hart, Loughborough, all of United Kingdom

[73] Assignee: BG plc, Reading, United Kingdom

[21] Appl. No.: 09/068,132

[22] PCT Filed: Nov. 1, 1996

[86] PCT No.: PCT/GB96/02693

§ 371 Date: Sep. 14, 1998

§ 102(e) Date: Sep. 14, 1998

[87] PCT Pub. No.: WO97/16553

PCT Pub. Date: May 9, 1997

[30] Foreign Application Priority Data

Nov. 1, 1995 [GB] United Kingdom .................. 9522407
Nov. 2, 1995 [WO] WIPO ...................... PCT/GB9502588

[51] Int. Cl.[7] .............................. C12N 9/02; C12N 15/00; C12N 15/53; C12N 15/78
[52] U.S. Cl. ................. 435/189; 435/69.1; 435/252.3; 435/320.1; 435/471; 536/23.2
[58] Field of Search .................................. 435/69.1, 189, 435/252.3, 252.33, 320.1, 471; 536/23.2

[56] References Cited

FOREIGN PATENT DOCUMENTS 2294692  5/1996  United Kingdom .
WO95/16041  6/1995  WIPO .
WO 95/34679  12/1995  WIPO .
WO 96/14419  5/1996  WIPO .

OTHER PUBLICATIONS

Smith, C. A. D., et al., 1992, "Debrisoquine hydroxylase gene polymorphism and susceptibilty to Parkinson's disease", The Lancet, vol. 339, pp. 1375–1377.

Tuck, S. F., et al., 1993, "Active sites of the cytochrome p450cam (CYP101) F87W and F87A mutants", The Journal of Biological Chemistry, vol. 268, pp. 269–275.

Dawson, E., et al., 1994, "An association study of debrisoquine hydroxylase (CYP2D6) polymorphisms in schizophrenia", Psychiatric Genetics, vol. 4, pp. 215–218.

J. Biological Chemistry, Dec. 15, 1988, vol. 263 No.35, pp. 18842–18849; William M. Atkins et al., "The Roles of Active Site Hydrogen Bonding in Cytochrome P450cam as Revealed by Site–directed Mutagenesis."

J. AM. Chem. Soc., 1989, vol 111, No. 7, pp. 2715–2717; William M. Atkins et al., "Molecular Recognition in Cytochrome P–450: Alteration of Regioselective Alkane Hydroxylation via Protein Engineering."

J. Biological Chemistry, Apr. 5, 1990, vol. 265, No. 10, pp. 5361–5363; Carmelo Di Primo et al., "Mutagenesis of a Single Hydrogen Bond in Cytochrome P–450 Alters Cation Binding and Heme Solvation."

Primary Examiner—Ponnathapu Achutamurthy
Assistant Examiner—William W. Moore
Attorney, Agent, or Firm—William H. Holt

[57] ABSTRACT

A mutant of the mono-oxygenase cytochrome P450cam in which the cysteine residue at position 334 is removed.

13 Claims, 2 Drawing Sheets

MUTANT MONO-OXYGENASE CYTOCHROME P450CAM

The present invention relates to a mutant of the mono-oxygenase cytochrome P-450cam.

BACKGROUND OF THE INVENTION

Mono-oxygenases catalyse the selective oxidation of activated and unactivated carbon-hydrogen bonds using oxygen[1], and are therefore of great interest for potential use in organic synthesis. However, progress in this area has been hampered by the difficulty in isolating sufficient quantities of the mono-oxygenase enzyme and/or the associated electron-transfer proteins. Despite the availability of amino acid sequences of more than 150 different cytochrome P-450 mono-oxygenases, to date structural date of only three are available[2,3,4], and few have been successfully over-expressed in bacterial systems[5].

One cytochrome P-450 mono-oxygenase, which is soluble and can be expressed in sufficient quantities, is the highly specific P-450cam from *P. putida* which catalyses the regio- and stereo-selective hydroxylation of camphor to 5-exo-hydroxycamphor[6]. The high resolution crystal structure of P-450cam has been determined[2], and since the mechanism of action of this bacterial enzyme is believed to be very similar to that of its mammalian counterparts, it has been used as a framework on which structural models of mammalian enzymes are based.

The nucleotide sequence and corresponding amino acid sequence of P-450cam have been described[5,7]. The location of an active site of the enzyme is known and structure-function relationships have been investigated[8,9]. Mutants of P-450cam have been described at the 101 and 185 and 247 and 295 positions[9,10,11] and at the 87 position[12]. A mutant in which tyrosine 96 (Y96) has been changed to phenylalanine 96 (the Y96F mutant) has been described[11,13,14,15]. But in all cases the papers report effects of the mutations on the oxidation reactions of molecules which had previously been shown to be substrates for the wild-type enzyme. There is no teaching of how mutations might be used to provide biocatalysts for oxidation of different, novel substrates.

SUMMARY OF THE INVENTION

In an attempt to develop new biocatalysts, we have initiated a project which aims to redesign P-450cam, such that it is able more effectively to carry out specific oxidations of organic molecules whether or not these are substrates for the wild-type protein.

Figure 1:
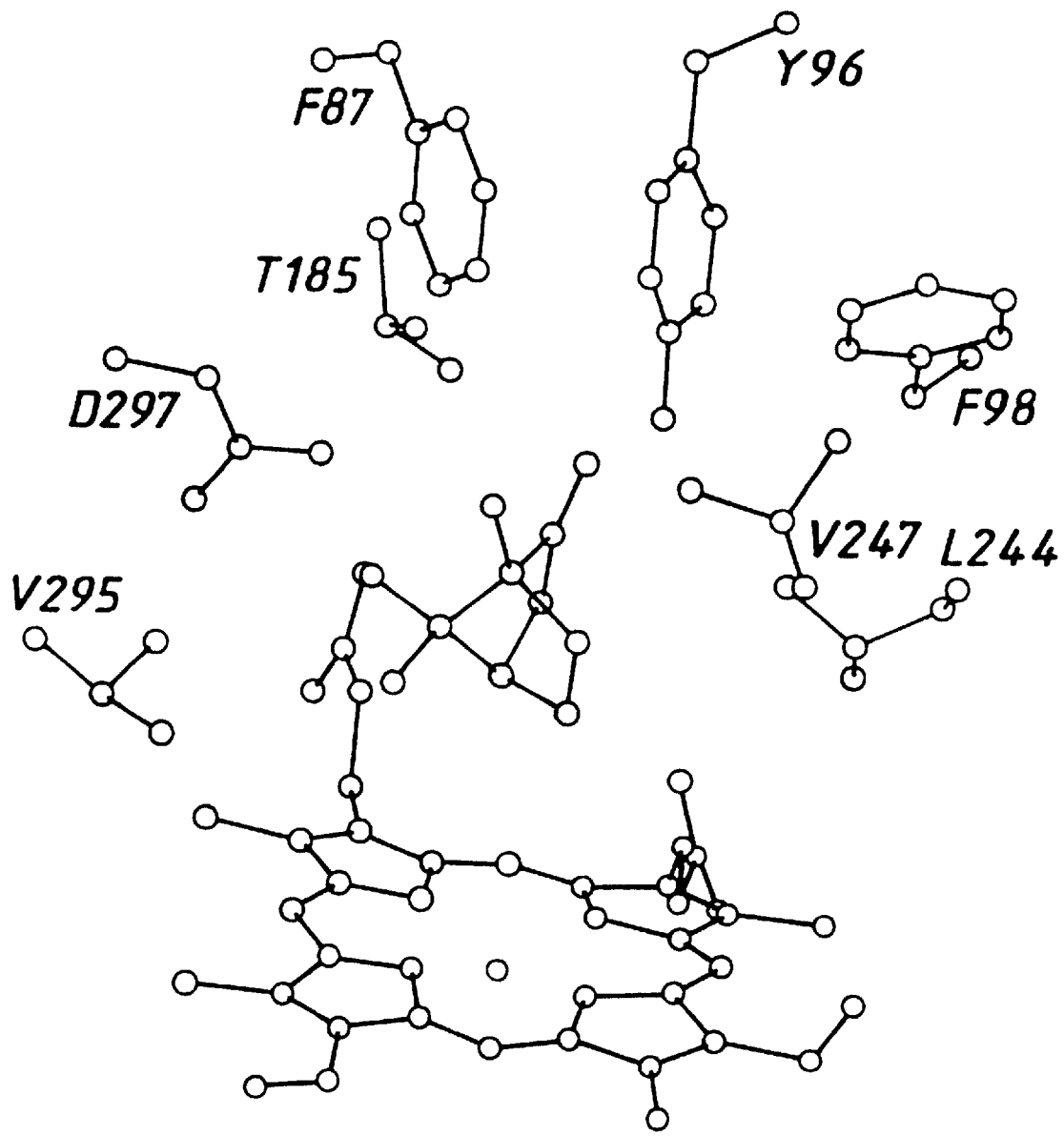
FIG. 1 illustrates that the three dimensional structure of P-450cam shows the active site to provide close van der Waals contact with the hydrophobic groups of camphor.

The three dimensional structure of P-450cam shows the active site to provide close van der Waals contacts with the hydrophobic groups of camphor as shown in FIG. 1. Of particular significance are the contacts between camphor and the side chains of leucine 244, valine 247 and valine 295. Three aromatic residues (Y96, F87 and F98) are grouped together and line the substrate binding pocket, with a hydrogen bond between tyrosine 96 and the camphor carbonyl oxygen maintaining the substrate in the correct orientation to ensure the regio- and stereo-specificity of the reaction.

Lipscomb and co-workers[16] demonstrated in 1978 that wild-type P-450cam showed a propensity to dimerise, but they also reported that the catalytic activity of the monomer and dimer towards camphor oxidation were indistinguishable. Since the dimerisation reaction could be reversed by thiol reducing agents, they concluded that it occurred by intermolecular cysteine disulphide (S—S) bond formation. They were unable to determine whether dimerisation involved more than one cysteine per P-450cam molecule. Nor were they able to identify the key cysteine residue(s) involved in this reaction because neither the amino acid sequence nor crystal structure of P-450cam were known at the time.

We used molecular modelling to investigate the likely effects of points mutations to the three aromatic residues (Y96, F87, F98) in the active site pocket. We noted that replacement of any of these aromatic residues with a smaller, hydrophobic non-aromatic side-chain could provide an "aromatic pocket" which could be used to bind more hydrophobic substrates. The program GRID[17] was used to calculate an energy of interaction between an aromatic probe and possible mutants of cytochrome P-450cam where these residues were changed to alanine (F87A, Y96A and F98A). The results were then examined graphically using the molecular modelling package Quanta[18].

The mutant F98A appeared to have the strongest binding interaction within the active site cavity accessible to the aromatic probe, with that of Y96A being slightly smaller, and that of F87A being substantially less. It was decided in the first instance to mutate tyrosine 96 to alanine as it is more central to the binding pocket, whereas phenylalanine 98 is in a groove to one side. Also, removal of tyrosine 96 should decrease the specificity of the enzyme towards camphor due to the loss of hydrogen bonding to the substrate.

According to one aspect of the present invention a mutant of the mono-oxygenase cytochrome p-450cam is provided in which the cysteine residue at position 334 is removed.

Preferably the removal is by the substitution of another amino acid except cysteine for the cysteine residue.

Alternatively the removal is by the deletion of the entire cysteine 344 residue from the enzyme.

Suitably the tyrosine residue at position 96 in the mutant is replaced by the residue of any amino acid except tyrosine.

Conveniently the amino acid is selected from any one of the following: alanine, arginine, asparagine, aspartic acid, cysteine, glutamic acid, glutamine, glycine, histidine, isoleucine, leucine, lysine, methionine, proline, serine, threonine, tryptophan, tyrosine and valine except that in the case of the cysteine residue at position 334, the amino acid is not cysteine and in the case of the tyrosine residue at position 96 the amino acid is not tyrosine.

Preferably the amino acid residue at one or more of the positions 87, 98, 101, 185, 193, 244, 247, 295, 297, 395 and 396 is replaced by another amino acid residue.

We examined the structure of P-450cam generated from the published crystallographic atomic co-ordinates using the modelling programme Quanta. We determined that there are five cysteines near the surface of P-450cam (cysteines 58, 85, 136, 148, 334) which might participate in intermolecular disulphide bond formation leading to protein dimerisation. We carried out sit-directed mutagenesis to substitute each of these cysteines to alanine, thus generating five Cys-Ala surface mutants.

Figure 2:
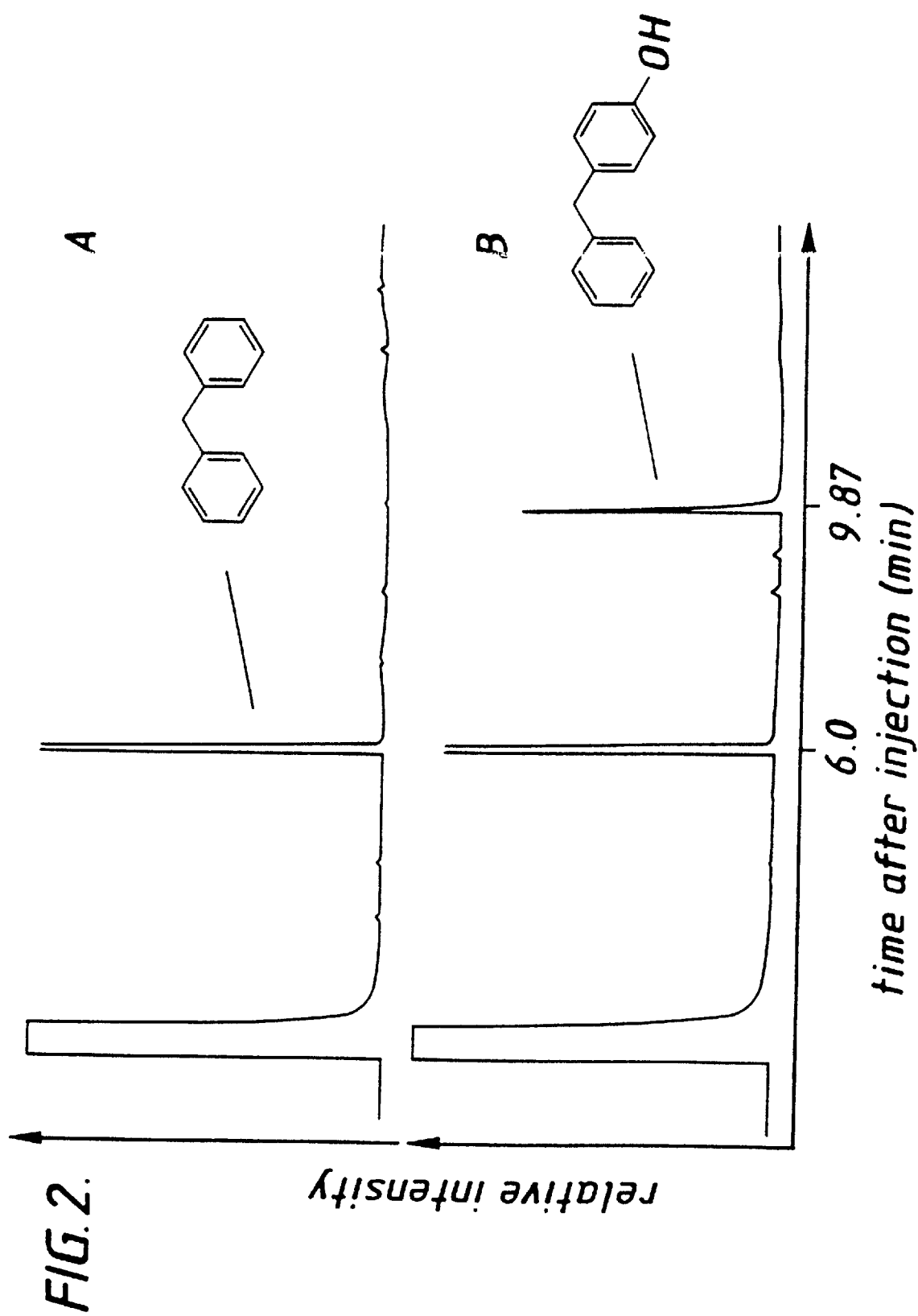
FIG. 2A and FIG. 2B are gas chromatographs in accord with the present invention.

The extent of protein dimerisation in the wild-type P-450cam and the five surface Cys-Ala mutants were investigated, The presence of dimer was detected by both anion exchange fast protein liquid chromatography on a Resource Q column (Pharmacia) and gel filtration size exclusion chromatography on a Superose 12 column (Pharmacia) in the wild-type P-450cam and the C58A, C85A, C136A and C148A mutants. On the other hand, no dimer was detected, even at high concentrations (0.1 mM range), for the C334A mutant (see data in FIG. 2). We concluded that wild-type P-450cam underwent dimerisation by intermolecular S—S disulphide bond formation between the surface cysteine 334 on two protein molecules.

The C334A mutation has the obvious benefit of removing unwanted protein dimerisation, thus ensuring the presence of a single species in solution at all times. In addition, we noted a completely unexpected benefit of this mutation. Like all proteins, wild-type P-450cam shows aggregation upon standing. The reasons why proteins aggregate are not clear, but the P-450cam aggregates are insoluble and catalytically inactive. The wild-type and C58A, C85A, C136A and C148A mutants all showed dimerisation as well as aggregation upon storage at 4° C., and even in 50% glycerol solutions at −20° C. Aggregation will also occur during turnover, especially at the higher P-450cam concentrations required in any economically viable industrial application in, for example, synthesis of organic molecules. The C334A mutant did not show any evidence of aggregation even at mM concentrations at room temperature over a period of three days. Thus, the C334A mutation has beneficial effects in protein handling, storage, and increased catalyst lifetime.

We believe the mutation at position 96 to be the key which enables the mutant enzymes to catalyse the oxidation of a relatively wide range of organic substrates. Other amino acids adjacent to the active site of the enzyme may also be mutated in order to change the shape and specificity of the active site. These other amino acids include those at positions 87, 98, 101, 185, 193, 244, 247, 295, 297, 395 and 396. It is envisaged that the amino acid at one or more of these positions may be replaced by: a small hydrophobic amino acid so as to enlarge the active site; or a large hydrophobic amino acid so as to reduce the size of the active site; or by an amino acid having an aromatic ring to interact with a corresponding aromatic ring of a substrate.

Regarding the oxidation reactions, the conditions are described in the literature references attached. The enzyme system typically includes putidaredoxin and putidaredoxin reductase together with NADH as co-factors in addition to the mutant enzyme. The example of cyclohexylbenzene oxidation is described in the experimental section below. Various classes of organic compounds are envisaged and described below. We note that the wild-type P-450cam is active towards the oxidation of a number of molecules included in the following sections. However, in all cases the mutant P-450cam proteins show much higher turnover activities.

i) The organic compound is an aromatic compound, either a hydrocarbon or a compound used under conditions in which it does not inactivate or denature the enzyme. Since the mutation has been effected with a view to creating an aromatic-binding pocket in the active site of the enzyme, the mutant enzyme is capable of catalysing the oxidation of a wide variety of aromatic compounds. Oxidation of example aromatic and polyaromatic compounds is demonstrated in the experimental section below and is believed very surprising given that the wild-type enzyme has been reported to catalyse the oxidation of only members of the camphor family and shows low activity towards a few other molecules such as styrene[19], ethylbenzene[9,10], a tetralone derivative[20], and nicotine[21].

ii) The organic compound may be a hydrocarbon, e.g. aliphatic or alicyclic, carrying a functional group (see Scheme 1). An aromatic protecting group is attached to the functional group prior to the oxidation reaction and removed from the functional group after the oxidation reaction. A suitable aromatic group is a benzyl group. The protecting group serves two purposes: firstly it makes the substrate more hydrophobic and hence increases binding to the hydrophobic enzyme pocket; secondly it may help to hold the substrate in place at the active site. Thus, with the correct aromatic protection group, both regio- and stereo-selective hydroxylation of the substrate may be achieved. Examples of mono-functionalised hydrocarbons are cyclohexyl, cyclopentyl and alkyl derivatives (Scheme 1). The oxidation products of these compounds are valuable starting materials for organic synthesis, particularly when produced in a homochiral form. A range of aromatic protecting groups are envisaged, e.g. benzyl or naphthyl ethers and benzoyl ethers and amides (Scheme 1). Of interest are also benzoxazole groups as carboxyl protecting groups and N-benzyl oxazolidine groups as aldehyde protecting groups. Both can be easily cleaved after the enzymatic oxidation and have previously been described in the literature for the microbial oxidations of aldehydes and acids[22].

iii) The organic compound is a C4 to C12 aliphatic or alicyclic hydrocarbon. Oxidation of cyclohexane and linear and branched hydrocarbons is demonstrated in the experimental section below. We have found that wild-type P-450cam is also capable of oxidising these molecules, but the activities are low and in all cases the mutants show substantially higher activities.

iv) The organic compound is a halogenated aliphatic or alicyclic hydrocarbon. Oxidation of lindane (hexachlorocyclohexane) is also describe below.

Mutants were constructed in which active site substitutions were combined with the surface mutation of cysteine at position 334 to alanine and contained alanine, leucine, valine, or phenylalanine instead of tyrosine at position 96 (Y96). Lastly several active site mutations and the surface mutation were combined to constitute mutant enzymes with multiple mutations. The genes encoding cytochrome P-450cam, and its natural electron-transfer partners putidaredoxin and putidaredoxin reductase, were amplified from the total cellular DNA of *P. Putida* using the polymerise chain reaction (PCR). The expression vector/*E. coli* host combinations employed were pRH1091[23] in strain JM109 for P-450cam, pUC 118 in strain JM109 for putidaredoxin, and pGL W11 in strain DH5 for putidaredoxin reductase. Oligonucleotide-directed site-specific mutagenesis was carried out using an M13 mp 19 subclone by the method of Zoller and Smith[24], and mutant selection was by the method of Kunkel[25].

Binding of potential substrates was investigated by spectroscopic methods. The wild-type enzyme in the absence of substrate is in the 6-co-ordinated, low-spin form with a weakly bound water occupying the sixth co-ordination site, and shows a characteristic Soret maximum at 418 nm. Binding of camphor and the substrate analogues adamantanone, adamantane and norbornane fully converted the haem to the 5-co-ordinated, high-spin form which has a characteristic Soret band at 392 nm. This haem spin-state shift is accompanied by an increase in the haem reduction potential which enables the physiological electron-transfer partner putidaredoxin to reduce P-450cam and initiate the catalytic hydroxylation cycle[26]. The haem spin state shift is thus a qualitative indication of the likelihood of molecules shown in Tables 1 and 2 being oxidised by the wild-type and mutant P-450cam enzymes.

A buffered solution (50 mM Tris.HCl, pH 7.4), typically 3 ml in volume, containing 10 uM putidaredoxin, 2 uM putidaredoxin reductase, 1 uM cytochrome P-450cam mono-oxygenase (wild-type or mutant), 200 mM KCl, 50 ug/ml bovine liver catalase (Sigma), and 1 mM target organic compound such as cyclohexylbenzene (added as a 0.1 M stock in ethanol) was preincubated at 30° C. for 5 minutes. The enzymatic reaction was initiated by adding NADH to a total concentration of 2 mM. Further four aliquots of NADH (to increase the NADH concentration by 1 mM each time) were added in intervals of 10 minutes, and 30 minutes into the incubation one aliquot of substrate (to increase the concentration by 1 mM) was also added. The reaction was quenched after 60 minutes by adding 0.5 ml chloroform and vortexing the mixture. The phases were separated by centrifugation (4000 g) at 4° C. The chloroform layer was analyzed by gas chromatography.

For many substrate compounds such as cyclohexylbenzene for which not all the P-450cam-mediated oxidation products are commercially available, the chloroform extracts are evaporated to dryness under a stream of nitrogen. The residues were extracted with hexane and the oxidation products separated by high performance liquid chromatography, eluting with a hexane/isopropanol gradient. The purified products were then identified by mass spectroscopy and particularly nuclear magnetic resonance spectroscopy.

For different substrates of different solubility in the aqueous buffer solution, the amount of substrate added to the incubation mixtures varies from 0.2 mM to 4 mM final concentration. The NADH concentration can be monitored at 340 nm and, in all cases, more substrates and NADH are added during the incubation.

Using the above experimental techniques, the inventors have investigated a considerable number of organic compounds as substrates for both the wild-type P-450cam enzyme and also the mutant version Y96A. Work has included mutants designated Y96V; Y96L; Y96f: C334A; the combined mutant F87A-Y96G-F193A and the combined active site and surface mutants of Y96A-C334A; Y96V-C334A; Y96L-C334A; Y96F-C334A; F87A-Y96G-F193A-C334A. The results for C334A and C334A-Y96A are set out in Table 1 and 2, in which structurally related molecules are grouped together.

Table 1 details the NADH consumption for oxidation of small linear, branched and cyclic hydrocarbons by the mutant Y96A-C334A. Tables 2(a) to 2(h) details the product distributions for mutant and substrate combinations where these have been elucidated to date.

The cysteine residue at position 344 can be deleted by any well known and freely available standard restriction techniques and will therefore not be described in detail herein.

Scheme 1:
Hydrocarbons

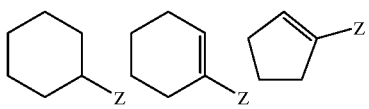

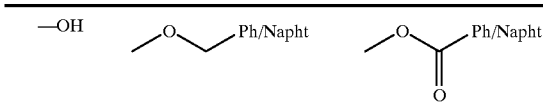

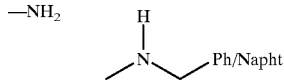

—Z     Protecting Group

—OH

—NH$_2$

-continued

Scheme 1:
Hydrocarbons

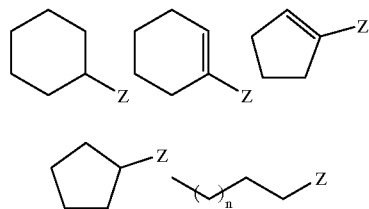

—Z     Protecting Group

—COOH

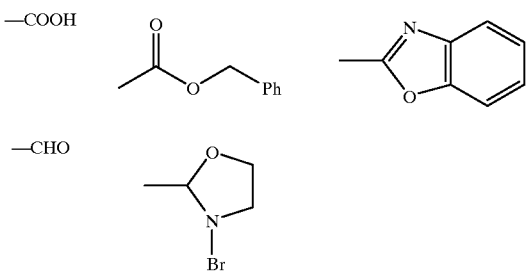

—CHO

TABLE 1

| | $K_{app}$ ($\mu$M)[a] | |
|---|---|---|
| | WT | Y96A |
| 1 | 6.3 | 12 |
| 2 | 12 | 28 |
| 3 | 8.4 | 1.4 |
| 4 | 330 | 92 |
| 5 | >1500[b] | 73 |

[a]Values are the average of two independent measurements using the method of Sligar (S. G. Sligar, Biochemistry, 1976, 15, 5399–5406). The value of $K_{app}$ is strongly dependent on the concentration of $K^+$ in the buffer. At [$K^+$] >150 mM, $K_{app}$ for camphor is 0.6 $\mu$M for both wildtype and Y96A. Data in this table were determined at [$K^+$] = 70 mM in phosphate buffer, pH 7.4, in order to avoid salting out of substrates at higher ion concentrations.
[b]Saturation not reached.

TABLE 2(a)
| P450cam-substrate interactions Subgroup: 1-ring | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
|  | Benzene | — | — | — | — | | | | |
| 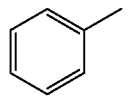 | Toluene | — | — | 30 | 30 | | | | |
| 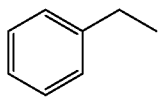 | Ethylbenzene | — | — | 40 | | | | | |
| 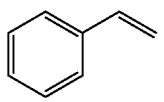 | Styrene | — | — | 30 | 30 | | | | |
|  | Cyclohexene | — | 5 | 40 | 40 | | | | |
|  | 1,3-Cyclohexadiene | nd | nd | nd | nd | | | | |
|  | 1,4-Cyclohexadiene | — | 5 | 15 | 20 | | | | |
|  | Cyclohexane | — | — | 60 | 60 | | | + | |
| 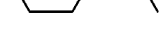 | Hexane | — | — | 70 | 60 | | | + | |
| 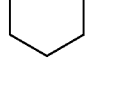 | Methylcyclohexane | 50 | 50 | 100 | 70 | | | | |
| 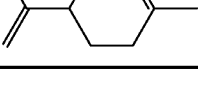 | (S)-(+)-Carvone | 10 | 60 | 10 | 80 | | | | |

TABLE 2(b)
| P450cam-substrate interactions Subgroup: 2-ring, Naphthalene | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 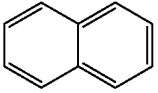 | Naphthalene | — | — | 15 | 20 | | | | |
| 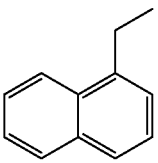 | 1-Ethylnaphthalene | — | — | 5 | 20 | | | | |
| 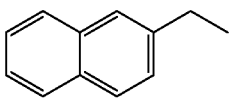 | 2-Ethylnaphthalene | — | — | 10 | 20 | | | | |
| 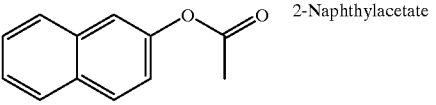 | 2-Naphthylacetate | — | 5 | — | 5 | | | | |
| 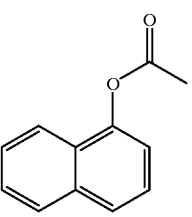 | 1-Naphthylacetate | — | 5 | — | 5 | | | | |
| 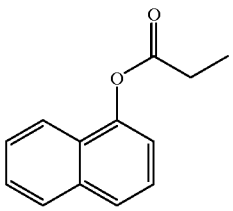 | 1-Naphthylpropionate | — | 20 | 0 | 20 | | | | |
| 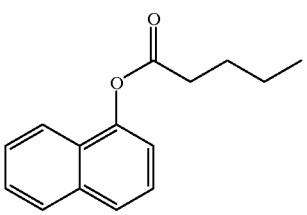 | 1-Naphthylbutyrate | — | 5 | — | 5 | | | | |
| 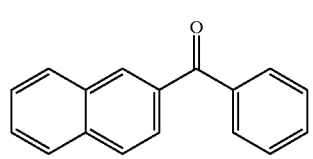 | Naphthylphenylketone | — | 5 | — | 5 | | | | |
| 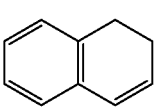 | 1,2-Dihydronaphthalene | 5 | 20 | 30 | 90 | | | | |

TABLE 2(b)-continued

| P450cam-substrate interactions Subgroup: 2-ring, Naphthalene | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 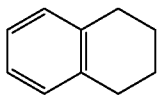 | 1,2,3,4-Tetrahydro naphthalene | 5 | 10 | 40 | 40 | | | | |

TABLE 2(c)

| P450cam-substrate interactions Subgroup: 2-ring, DPM | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 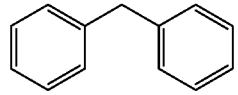 | Diphenylmethane | — | 5 | 45 | nd | | | + | + |
| 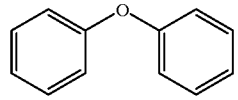 | Diphenylether | 10 | 5 | 20 | 50 | | | | |
| 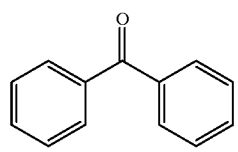 | Benzophenone | — | 20 | — | 20 | | | | |
| 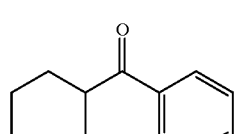 | Cyclohexylphenylketone | — | 30 | 60 | nd | | | | |
| 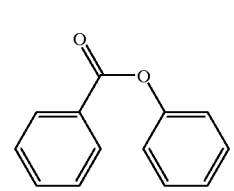 | Phenylbenzoate | — | 5 | — | — | | | | |
| 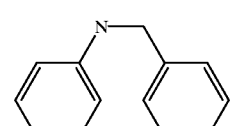 | N-Phenylbenzylamine | | 5 | 45 | nd | | | | |
| 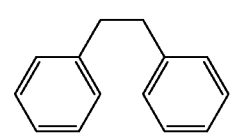 | Bibenzyl | — | — | 55 | 55 | | | | |

TABLE 2(c)-continued

| P450cam-substrate interactions Subgroup: 2-ring, DPM | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 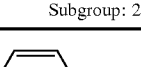 | cis-Stilbene | — | 20 | 40 | 50 | | | | |
| 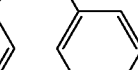 | Biphenyl | — | 20 | — | 90 | | | | |
| 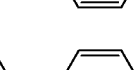 | Cyclohexylbenzen | 20 | 20 | 80 | nd | | | | |
| 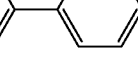 | trans-Stilbene | — | — | — | — | | | | |
| 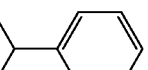 | Benzylether | — | 5 | 55 | nd | | | | |

TABLE 2(d)

| P450cam-substrate interactions Subgroup: 3-ring | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 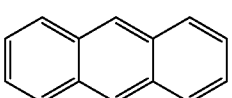 | Anthracene | | | | | | | | |
| 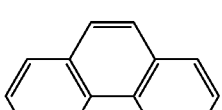 | Phenanthrene | — | — | 20 | 20 | | | + | |
| 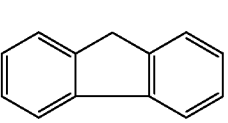 | Fluorene | — | — | — | 50 | | | | |
| 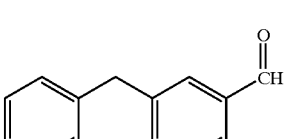 | 2-Fluorencarboxaldehyde | — | — | — | 50 | | | | |

TABLE 2(d)-continued

| P450cam-substrate interactions<br>Subgroup: 3-ring | | Wild type ΔSpin high/low | Wild type Vs DTT | Mutant Y96A ΔSpin high/low | Mutant Y96A Vs DTT | Wild type NADH turnover? | Wild type GC? | Mutant Y96A NADH turnover? | Mutant Y96A GC? |
|---|---|---|---|---|---|---|---|---|---|
| 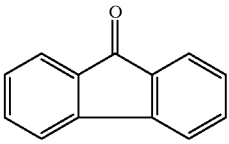 | 9-Fluorenone | — | 20 | — | 5 | | | | |
| 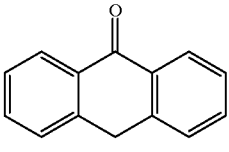 | Anthrone | — | 5 | — | 5 | | | | |
| 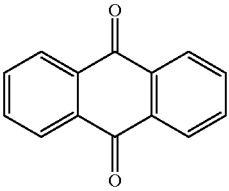 | Anthraquinone | | | | | | | | |
| 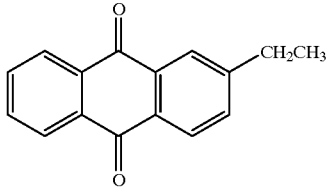 | 2-Ethylanthraquinone | | | | | | | | |

TABLE 2(e)

| P450cam-substrate interactions<br>Subgroup: 4,5-ring | | Wild type ΔSpin high/low | Wild type Vs DTT | Mutant Y96A ΔSpin high/low | Mutant Y96A Vs DTT | Wild type NADH turnover? | Wild type GC? | Mutant Y96A NADH turnover? | Mutant Y96A GC? |
|---|---|---|---|---|---|---|---|---|---|
| 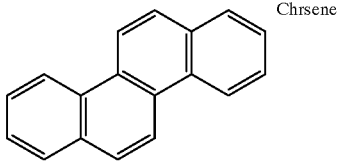 | Chrsene | — | — | — | — | | | | |
| 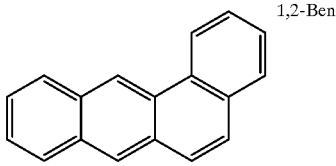 | 1,2-Benzanthracene | — | — | — | — | | | | |

TABLE 2(e)-continued

| P450cam-substrate interactions Subgroup: 4,5-ring | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 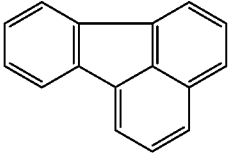 | Fluoranthene | — | 5 | 20 | 10 | | | | |
| 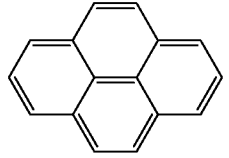 | Pyrene* | — | — | — | — | | | | |
| 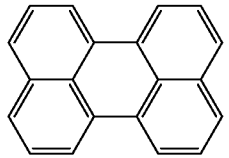 | Perylene* | — | — | — | — | | | | |

TABLE 2(f)

| P450cam-substrate interactions Subgroup: Cyclic Alkanes | | Wild type | | Mutant Y96A | | Wild type | | Mutant Y96A | |
|---|---|---|---|---|---|---|---|---|---|
| | | ΔSpin high/low | Vs DTT | ΔSpin high/low | Vs DTT | NADH turnover? | GC? | NADH turnover? | GC? |
| 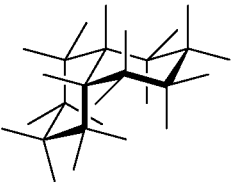 | cis-Decahydronaphthalene | nd | nd | nd | nd | | | | |
| 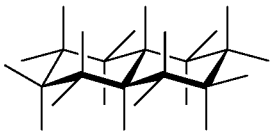 | trans-Decahydro naphthalene | 20 | 10 | 90 | 70 | | | | |
| 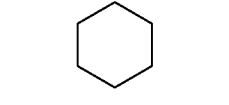 | Cyclohexane | — | — | 60 | 60 | | | | + |
| 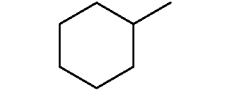 | Methylcyclohexane | 50 | 50 | 100 | 70 | | | | |

TABLE 2(g)

| P450cam-substrate interactions Subgroup: n-Alkanes | | Wild type ΔSpin high/low | Wild type Vs DTT | Mutant Y96A ΔSpin high/low | Mutant Y96A Vs DTT | Wild type NADH turnover? | Wild type GC? | Mutant Y96A NADH turnover? | Mutant Y96A GC? |
|---|---|---|---|---|---|---|---|---|---|
| | n-Pentane | — | 5 | 55 | 40 | | | + | |
| | n-Hexane | — | — | 60 | 40 | | | + | |
| | n-Heptane | 5 | 5 | 60 | 40 | | | + | |
| | n-Octane | — | 5 | 80 | 45 | | | + | |
| | n-Nonane | — | — | 70 | 45 | | | + | |
| | n-Decane | nd | nd | nd | nd | | | | |
| | n-Undecane | nd | nd | 20 | 20 | | | | |
| | n-Dodecane | nd | nd | 5 | 5 | | | | |
| $CH_3(CH_2)_{14}CH_3$ | n-Hexadecane | — | — | — | — | | | | |
| $CH_3(CH_2)_{15}CH_3$ | n-Heptadecane | — | — | — | — | | | | |
| $CH_3(CH_2)_{11}OSO_3.Na$ | SDS | — | 20 | — | 60 | | | | |
| $CH_3(CH_2)_7CH{=}CH(CH_2)_7CO_2H$ | Oleic acid* | — | 10? | — | 20? | | | | |
| $[(CH_3)_2CH(CH_2)_3CH(CH_3)(CH_2)_3CH(CH_3)CH_2CH_2{-}]_2$ | Squalane | — | — | — | 20 | | | | |
| 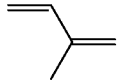 | Isoprene | — | — | 10 | 10 | | | | |

TABLE 2(h)

| P450cam-substrate interactions Subgroup: Camphor-like | | Wild type ΔSpin high/low | Wild type Vs DTT | Mutant Y96A ΔSpin high/low | Mutant Y96A Vs DTT | Wild type NADH turnover? | Wild type GC? | Mutant Y96A NADH turnover? | Mutant Y96A GC? |
|---|---|---|---|---|---|---|---|---|---|
| 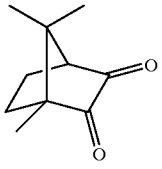 | (1R)-(−)-Camphorquinone | 80 | 80 | 80 | 80 | | | | |
| 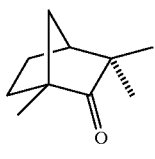 | (1R)-(−)-Fenchone | 40 | 70 | 50 | 80 | | | | |
| 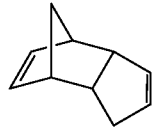 | Dicyclopentadiene | 50 | 80 | 90 | 90 | | | | |

TABLE 3

Turnover of Small Alkanes by P450cam Mutants
All mutants listed below also contain the C334A mutation.
Turnover rate measured as NADH consumption rate
(nmole NADH/nmole P450cam/s).

Alkane substrate:

| Main chain length | Name | Wild type | Y96A |
|---|---|---|---|
| C4 | n-butane | — | — |
| C4 | 2-methyl butane | background | 4.6 |
| C4 | 2,3-dimethyl butane | background | 16.8 |
| C4 | 2,2-dimethyl butane | background | 14.0 |
| C5 | n-pentane | background | 5.8 |
| C5 | 2-methyl pentane | 3.8 | 11.7 |
| C5 | 3-methyl pentane | 1.3 | 14.2 |
| C5 | 2,4-dimethyl pentane | 0.2 | 12.6 |
| C5 | 2,2-dimethyl pentane | 5.2 | 12.8 |
| C5 | 2,2,4-trimethyl pentane | 0.9 | 5.3 |
| C5 | 3-ethyl pentane | background | 16.2 |
| C6 | n-hexane | background | 6.0 |
| C6 | 2-methyl hexane | background | 10.6 |
| C7 | n-heptane | 2.7 | 4.4 |
| C7 | 2-methyl heptane | background | 2.1 |
| C7 | 4-methyl heptane | 1.4 | 10.2 |
| C8 | n-octane | background | 5.8 |
| C7 | cycloheptane | 4.4 | 42.5 |

Product structures and distributions following oxidation of substrates with P450cam active site mutants.
"background" - typical background NADH oxidation rate is 0.07 nmole NADH (nmole P450cam)$^{-1}$ sec$^{-1}$

TABLE 4(a)

Product structure and distributions following oxidation of substrates with P450cam active site mutants. All mutants shown below also contain the C334A mutation.

| Cyclohexylbenzene Products | | | Products (%) for mutants: | | | | |
|---|---|---|---|---|---|---|---|
| | | | WT | Y96A | Y96F | Y96L | Y96V |
| 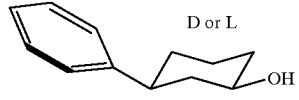 D or L | 3-ol | | 43 | 20 | 54 | 38 | 28 |
| 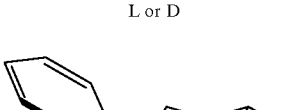 L or D | 3-ol | | 20 | 20 | 27 | 23 | 39 |
| 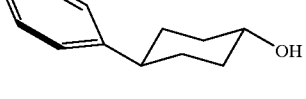 | Trans-4-ol | | 25 | 15 | 6 | 23 | 10 |
| 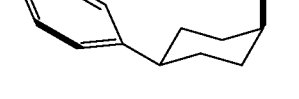 | Cis-4-ol | | 12 | 45 | 13 | 16 | 23 |
| Total products(area/10$^5$) | | | 0.8 | 7.4 | 1.1 | 10.4 | 12.5 |

Cyclohexylbenzene

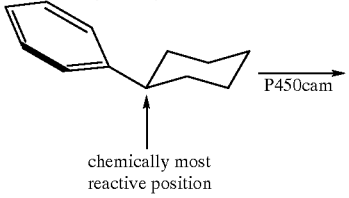

chemically most reactive position

TABLE 4(a)-continued

Product structure and distributions following oxidation of substrates with P450cam active site mutants. All mutants shown below also contain the C334A mutation.

| Cyclohexylbenzene Products | Products (%) for mutants: | | | | |
|---|---|---|---|---|---|
| | WT | Y96A | Y96F | Y96L | Y96V |

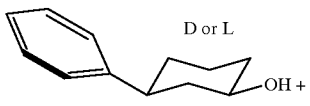

TABLE 4(b)

| Phenylcyclohexene Products | | Products (%) for mutants: | |
|---|---|---|---|
| | | WT | Y96A |
| 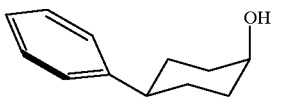 | 3-one (A) | 24 | 25 |
|  | 3-ol (B) | 76 | 75 |
| Total products(area/10⁶) | | 42 | 36 |

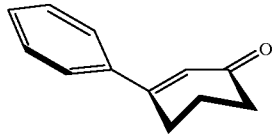

TABLE 4(b)-continued

| Phenylcyclohexene Products | Products (%) for mutants: | |
|---|---|---|
| | WT | Y96A |

TABLE 4(c)

| Naphthalene Products | | WT | Y96A | Y96F | Y96L | Y96V | F87A-F96G-F193A |
|---|---|---|---|---|---|---|---|
| 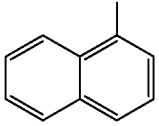 | 1-ol | 100 | 100 | 100 | 100 | 100 | 100 |
| 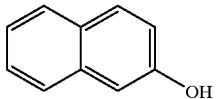 | 2-ol | 0 | 0 | 0 | 0 | 0 | 0 |
| Total products(area/$10^5$) | | (0.016) | 1.1 | 2.4 | 0.7 | 1.4 | 0.1 |

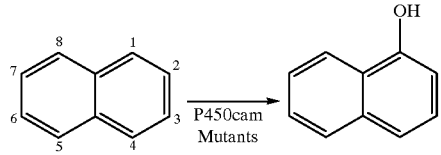

TABLE 4(d)

| Phenanthrene Products | WT | Y96A | Y96F | Y96L | Y96V | F87A-F96G-F193A |
|---|---|---|---|---|---|---|
| A | 38 | 49 | 41 | 35.5 | 41 | 27 |
| B | 15 | 23 | 31 | 41 | 38 | 41 |
| C | 12 | 13 | 5 | 9 | 11 | 3 |
| D | 35 | 15 | 23 | 14.5 | 10 | 29 |
| Total products (area/$10^6$) | 0.075 | 7.0 | 4.5 | 2.8 | 1.6 | 0.065 |

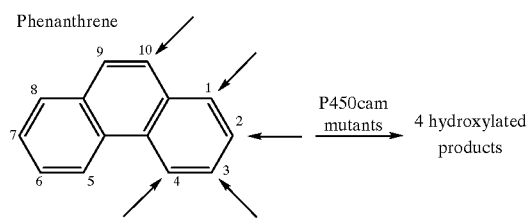

TABLE 4(e)

| Fluoranthene Products | WT | Y96A | Y96F | Y96L | Y96V | F87A-F96G-F193A |
|---|---|---|---|---|---|---|
| A | 0 | 84 | — | — | — | 0 |
| B | 0 | 16 | — | — | — | 100 |
| Total products (area/$10^6$) | 0 | 2.7 | — | — | — | 0.2 |

TABLE 4(e)-continued

| Fluoranthene Products | WT | Y96A | Y96F | Y96L | Y96V | F87A-F96G-F193A |
|---|---|---|---|---|---|---|

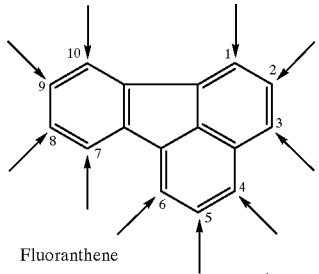

TABLE 4(f)

| Pyrene Products | WT | Y96A | Y96F | Y96L | Y96V | F87A-F96G-F193A |
|---|---|---|---|---|---|---|
| A | 0 | 40 | 43 | 23 | 30 | 33 |
| B | 0 | 43.6 | 29 | 64.5 | 55 | 40 |
| C | 0 | 5 | 12.5 | 7.9 | 12 | 20 |
| D | 0 | 11.4 | 15.5 | 4.6 | 3 | 7 |
| Total products (area/$10^6$) | 0 | 1.2 | 1.5 | 1.5 | 1.6 | 0.02 |

TABLE 4(f)-continued

| Pyrene Products | Products (%) for mutants: | | | | |
|---|---|---|---|---|---|
| | WT | Y96A | Y96F | Y96L | Y96V | F87A-F96G-F193A |

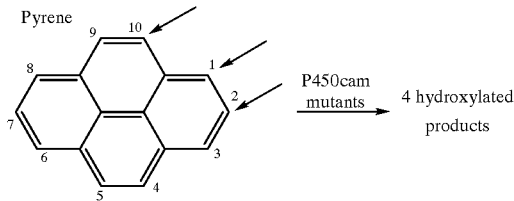

TABLE 4(g)

| Lindane Products | Products (%) for mutants | |
|---|---|---|
| (hexachlorocyclohexane) | WT | Y96A |
| A | 100 | 100 |
| Turnover rate nmole NADH (nmoleP450)$^{-1}$s$^{-1}$ | 7.5 | 43.5 |

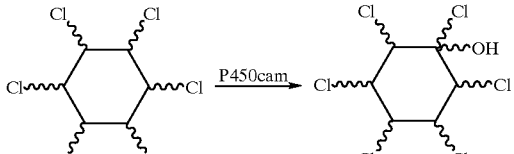

Hexachlorocyclohexane

TABLE 4(h)

| | Products(%) for mutants: | |
|---|---|---|
| | Y96F | Y96A |
| Hexane Products | | |
| 2-hexanone | 10 | 15 |
| 3-hexanone | 16 | 28 |
| 2-hexanol | 24 | 26 |
| 3-hexanol | 50 | 32 |
| Relative activity (WT = 1) | 18.2 | 25.5 |
| 2-Methyl hexane Products | | |
| 2-methyl-2-hexanol | 72 | 74 |
| 5-methyl-2-hexanone | 16 | 14 |
| 2-methyl-3-hexanol | 7 | 4 |
| 5-methyl-2-hexanol | 5 | 8 |
| Relative activity (WT = 1) | 2.3 | 2.6 |

REFERENCES

1. "Cytochroe P-450: Structure, Mechanism, and Biochemistry", ed. P R Ortiz de Montellano, Plenum Press, New York, 1986.
2. T L Poulos, B C Finzel and A J Howard, J. Mol. Biol., 1987, 195, 687–700.
3. C A Hasemann, K G Ravichandran, J A Peterson, and J Deisenhofer, J. Mol. Biol., 1994, 2–)6, 1169–1185.
4. K G Ravichandran, S S Boddupalli, C A Hasemann, J A Peterson, and J Deisenhofer, Science, 1993, 261, 731–736.
5. B P Unger, I C Gunsalus, and S G Sligar, J. Biol. Chem., 1986, 261, 1158–1163; J S Miles, A W Munro, B N Rospendowski, W E Smith, J McKnight, and A J Thomson, Biochem. J., 1992, 288, 503–509; T H Richardson, M J Hsu, T Kronbach, H J Bames, G Chan, M R Waterman, B Kemper, and E F Johnson, Arch. Biochem. Biophys., 1993, 300, 510–516; S S Boddupalli, T Oster, R W Estabrook, and J A Peterson, J. Biol. Chem., 1992, 267, 10375–10380; H Li K Darish and T L Poulos. J. Biol. Chem., 1991, 266, 11909–11914.
6. I C Gunsalus and G C Wagner, Methods Enzymol., 1978, 52, 166–188.
7. M Haniu, L G Armes, K T Yasunobu, B A Shastry, and I C Gunsalus. Biol. Chem., 1982, 257, 12664–12671.
8. S G Sligar, D Filipovic, and P S Stayton, Methods Enzymol., 1991, 206, 31–49.
9. P J. Loida and S G Sligar, Biochemistrv, 1993, 32, 11530–11538.
10. P J Loida and S G Sligar, Protein Eng., 1993, 6, 207–212.
11. W M. Atkins and S G Sligar, J. Am. Chem. Soc., 1989, 111, 2715–2717.
12. S F Tuck, S Graham-Lorence, J A Peterson, and P R Ortiz de Montellano, J. Biol. Chem., 1993, 268, 269–275.
13. C Di Prime, G Hui Bin Hoa, P. Douzou, and S Sligar, J. Biol. Chem., 1990, 265, 5361–5363.
14. W M Atkins and S G Sligar, J. Biol. Chem., 1988, 263, 18842–18849.
15. W M Atkins and S G Sligar, Biochemistry, 1990, 29, 1271–1275.
16. J D Lipscomb, J E Harrison, K M Dus, and I C Gunsalus, Biochem. Biophys. Res. Conunun., 1978, 83, 771–778.
17. P J Goodford, J. Med. Chem., 1985, 28, 849–857.
18. Quanta 4.0, Molecular Simulations Inc., 16 New England Executive Park, Burlington, Mass. 01803-5297.
19. J A Fruetet, J R Collins, D L Camper, G H Loew, and P R Ortiz de Montallano, J. Am. Chem. Soc., 1992, 114, 6987–6993.
20. Y Watanabe and Y Ishimura, J. Am. Chem. Sec., 1989, 111, 410–41 1.
21. J P Jones, W F Trager, and T J Carlson, J. Am. Chem. Soc., 1993, 115, 381–387.
22. "Biotransformation in Preparative Organic Chemistry" H G Davis, R H Green, D R Kelly, and S M Roberts, Academic Press, London, 1989, Page 169 ff.
23. J E Baldwin J M Blackburn, R J Heath, and J D Sutherland, Bioorg. Med. Chem. Letts. 1992, 2, 663–668.
24. M J Zoller and M Smith, Nucleic Acids Res., 1982, 10, 6487–6500.
25. T A Kunkel, Proc. Natl. Acad. Sci., USA 1985, 82, 488–492.
26. S G Sligar and I C Gunsalus, Proc. Natl. Acad. Sci., USA, 1976, 73, 1078–1082.

What is claimed is:

1. A mutant mono-oxygenase cytochrome P450cam comprising either a deletion of the cysteine at amino acid position 334 or a substitution of another amino acid for the cysteine at amino acid position 334.

2. A mutant mono-oxygenase cytochrome P450cam according to claim 1 wherein an amino acid other than cysteine is substituted at amino acid position 334.

3. A mutant mono-oxygenase cytochrome P450cam according to claim 2 further comprising the substitution of an amino acid other than tyrosine at amino acid position 96.

4. A mutant mono-oxygenase cytochrome $P^{450}$cam according to claim 2 further comprising one or more amino acid substitutions at amino acid positions selected from the group consisting of 87, 98, 101, 185, 193, 244, 247, 295, 297, 395, and 396.

5. A mutant mono-oxygenase cytochrome P450cam according to claim 1 wherein the cysteine is deleted at amino acid position 334.

6. A mutant mono-oxygenase cytochrome P450cam according to claim 5 further comprising the substitution of an amino acid other than tyrosine at amino acid position 96.

7. A mutant mono-oxygenase cytochrome P450cam according to claim 5 further comprising one or more amino acid substitutions at amino acid positions selected from the group consisting of 87, 98, 101, 185, 193, 244., 247, 295, 297, 395, and 396.

8. A mutant mono-oxygenase cytochrome P450cam according to claim 1 further comprising the substitution of an amino acid other than tyrosine at amino acid position 96.

9. A mutant mono-oxygenase cytochrome P450cam according to claim 8 wherein the substituent amino acid for position 96 is selected from the group consisting of alanine, arginine, asparagine, aspartic acid, glutamic acid, glutamine, glycine, histidine, isoleucine, leucine, lysine, methionine, proline, serine, threonine, tryptophan, tyrosine and valine.

10. A mutant mono-oxygenase cytochrome P450cam according to claim 8 further comprising one or more amino acid substitutions at amino acid positions selected from the group consisting of 87, 98, 101, 185, 193, 244, 247, 295, 297, 395, and 396.

11. A mutant mono-oxgenase cytochrome P450cam according to claim 1 wherein the substituent amino acid is selected from the group consisting of alanine, arginine, asparagine, aspartic acid, glutamic acid, glutamine, glycine, histidine, isoleucilne, leucine, lysine, methionine, proline, serine, threonine, tryptophan, tyrosine and valine.

12. A mutant mono-oxygenase cytochrome P450cam according to claim 11 further comprising one or more amino acid substitutions at amino acid positions selected from the group consisting of 87, 98, 101, 185, 193, 244, 247, 295, 297, 395, and 396.

13. A mutant mono-oxygenase cytochrome P450cam according to claim 1 further comprising one or more amino acid substitutions at amino acid positions selected from the group consisting of 87, 98, 101, 185, 193, 244, 247, 295, 297, 395, and 396.

* * * * *

SEQUENCE LISTING

<160> NUMBER OF SEQ ID NOS: 2

<210> SEQ ID NO 1
<211> LENGTH: 1242
<212> TYPE: DNA
<213> ORGANISM: Pseudomonas putida
<220> FEATURE:
<221> NAME/KEY: P450cam WT
<222> LOCATION: 1...1242

<400> SEQUENCE: 1

| | | | | | | | | | | | | | | | | |
|---|---|---|---|---|---|---|---|---|---|---|---|---|---|---|---|---|
| acg | act | gaa | acc | ata | caa | agc | aac | gcc | aat | ctt | gcc | cct | ctg | cca | ccc | 48 |
| Thr | Thr | Glu | Thr | Ile | Gln | Ser | Asn | Ala | Asn | Leu | Ala | Pro | Leu | Pro | Pro | |
| 1 | | | | 5 | | | | | 10 | | | | | 15 | | |
| cat | gtg | cca | gag | cac | ctg | gta | ttc | gac | ttc | gac | atg | tac | aat | ccg | tcg | 96 |
| His | Val | Pro | Glu | His | Leu | Val | Phe | Asp | Phe | Asp | Met | Tyr | Asn | Pro | Ser | |
| | | | 20 | | | | | 25 | | | | | 30 | | | |
| aat | ctg | tct | gcc | ggc | gtg | cag | gag | gcc | tgg | gca | gtt | ctg | caa | gaa | tca | 144 |
| Asn | Leu | Ser | Ala | Gly | Val | Gln | Glu | Ala | Trp | Ala | Val | Leu | Gln | Glu | Ser | |
| | | 35 | | | | | 40 | | | | | 45 | | | | |
| aac | gta | ccg | gat | ctg | gtg | tgg | act | cgc | tgc | aac | ggc | gga | cac | tgg | atc | 192 |
| Asn | Val | Pro | Asp | Leu | Val | Trp | Thr | Arg | Cys | Asn | Gly | Gly | His | Trp | Ile | |
| | 50 | | | | | 55 | | | | | 60 | | | | | |
| gcc | act | cgc | ggc | caa | ctg | atc | cgt | gag | gcc | tat | gaa | gat | tac | cgc | cac | 240 |
| Ala | Thr | Arg | Gly | Gln | Leu | Ile | Arg | Glu | Ala | Tyr | Glu | Asp | Tyr | Arg | His | |
| 65 | | | | | 70 | | | | | 75 | | | | | 80 | |
| ttt | tcc | agc | gag | tgc | ccg | ttc | atc | cct | cgt | gaa | gcc | ggc | gaa | gcc | tac | 288 |
| Phe | Ser | Ser | Glu | Cys | Pro | Phe | Ile | Pro | Arg | Glu | Ala | Gly | Glu | Ala | Tyr | |
| | | | | 85 | | | | | 90 | | | | | 95 | | |
| gac | ttc | att | ccc | acc | tcg | atg | gat | ccg | ccc | gag | cag | cgc | cag | ttt | cgt | 336 |
| Asp | Phe | Ile | Pro | Thr | Ser | Met | Asp | Pro | Pro | Glu | Gln | Arg | Gln | Phe | Arg | |
| | | | 100 | | | | | 105 | | | | | 110 | | | |
| gcg | ctg | gcc | aac | caa | gtg | gtt | ggc | atg | ccg | gtg | gtg | gat | aag | ctg | gag | 384 |
| Ala | Leu | Ala | Asn | Gln | Val | Val | Gly | Met | Pro | Val | Val | Asp | Lys | Leu | Glu | |
| | | 115 | | | | | 120 | | | | | 125 | | | | |
| aac | cgg | atc | cag | gag | ctg | gcc | tgc | tcg | ctg | atc | gag | agc | ctg | cgc | ccg | 432 |
| Asn | Arg | Ile | Gln | Glu | Leu | Ala | Cys | Ser | Leu | Ile | Glu | Ser | Leu | Arg | Pro | |
| | 130 | | | | | 135 | | | | | 140 | | | | | |
| caa | gga | cag | tgc | aac | ttc | acc | gag | gac | tac | gcc | gaa | ccc | ttc | ccg | ata | 480 |
| Gln | Gly | Gln | Cys | Asn | Phe | Thr | Glu | Asp | Tyr | Ala | Glu | Pro | Phe | Pro | Ile | |
| 145 | | | | | 150 | | | | | 155 | | | | | 160 | |
| cgc | atc | ttc | atg | ctg | ctc | gca | ggt | cta | ccg | gaa | gaa | gat | atc | ccg | cac | 528 |
| Arg | Ile | Phe | Met | Leu | Leu | Ala | Gly | Leu | Pro | Glu | Glu | Asp | Ile | Pro | His | |
| | | | | 165 | | | | | 170 | | | | | 175 | | |
| ttg | aaa | tac | cta | acg | gat | cag | atg | acc | cgt | ccg | gat | ggc | agc | atg | acc | 576 |
| Leu | Lys | Tyr | Leu | Thr | Asp | Gln | Met | Thr | Arg | Pro | Asp | Gly | Ser | Met | Thr | |
| | | | 180 | | | | | 185 | | | | | 190 | | | |
| ttc | gca | gag | gcc | aag | gag | gcg | ctc | tac | gac | tat | ctg | ata | ccg | atc | atc | 624 |
| Phe | Ala | Glu | Ala | Lys | Glu | Ala | Leu | Tyr | Asp | Tyr | Leu | Ile | Pro | Ile | Ile | |
| | | 195 | | | | | 200 | | | | | 205 | | | | |
| gag | caa | cgc | agg | cag | aag | ccg | gga | acc | gac | gct | atc | agc | atc | gtt | gcc | 672 |
| Glu | Gln | Arg | Arg | Gln | Lys | Pro | Gly | Thr | Asp | Ala | Ile | Ser | Ile | Val | Ala | |
| | 210 | | | | | 215 | | | | | 220 | | | | | |
| aac | ggc | cag | gtc | aat | ggg | cga | ccg | atc | acc | agt | gac | gaa | gcc | aag | agg | 720 |
| Asn | Gly | Gln | Val | Asn | Gly | Arg | Pro | Ile | Thr | Ser | Asp | Glu | Ala | Lys | Arg | |
| 225 | | | | | 230 | | | | | 235 | | | | | 240 | |
| atg | tgt | ggc | ctg | tta | ctg | gtc | ggc | ggc | ctg | gat | acg | gtg | gtc | aat | ttc | 768 |
| Met | Cys | Gly | Leu | Leu | Leu | Val | Gly | Gly | Leu | Asp | Thr | Val | Val | Asn | Phe | |
| | | | | 245 | | | | | 250 | | | | | 255 | | |

-continued

```
ctc agc ttc agc atg gag ttc ctg gcc aaa agc ccg gag cat cgc cag      816
Leu Ser Phe Ser Met Glu Phe Leu Ala Lys Ser Pro Glu His Arg Gln
        260                 265                 270 gag ctg atc gag cgt ccc gag cgt att cca gcc gct tgc gag gaa cta      864
Glu Leu Ile Glu Arg Pro Glu Arg Ile Pro Ala Ala Cys Glu Glu Leu
            275                 280                 285 ctc cgg cgc ttc tcg ctg gtt gcc gat ggc cgc atc ctc acc tcc gat      912
Leu Arg Arg Phe Ser Leu Val Ala Asp Gly Arg Ile Leu Thr Ser Asp
    290                 295                 300 tac gag ttt cat ggc gtg caa ctg aag aaa ggt gac cag atc ctg cta      960
Tyr Glu Phe His Gly Val Gln Leu Lys Lys Gly Asp Gln Ile Leu Leu
305                 310                 315                 320 ccg cag atg ctg tct ggc ctg gat gag cgc gaa aac gcc tgc ccg atg     1008
Pro Gln Met Leu Ser Gly Leu Asp Glu Arg Glu Asn Ala Cys Pro Met
                325                 330                 335 cac gtc gac ttc agt cgc caa aag gtt tca cac acc acc ttt ggc cac     1056
His Val Asp Phe Ser Arg Gln Lys Val Ser His Thr Thr Phe Gly His
            340                 345                 350 ggc agc cat ctg tgc ctt ggc cag cac ctg gcc cgc cgg gaa atc atc     1104
Gly Ser His Leu Cys Leu Gly Gln His Leu Ala Arg Arg Glu Ile Ile
        355                 360                 365 gtc acc ctc aag gaa tgg ctg acc agg att cct gac ttc tcc att gcc     1152
Val Thr Leu Lys Glu Trp Leu Thr Arg Ile Pro Asp Phe Ser Ile Ala
    370                 375                 380 ccg ggt gcc cag att cag cac aag agc ggc atc gtc agc ggc gtg cag     1200
Pro Gly Ala Gln Ile Gln His Lys Ser Gly Ile Val Ser Gly Val Gln
385                 390                 395                 400 gca ctc cct ctg gtc tgg gat ccg gcg act acc aaa gcg gta             1242
Ala Leu Pro Leu Val Trp Asp Pro Ala Thr Thr Lys Ala Val
                405                 410                 414
```

<210> SEQ ID NO 2
<211> LENGTH: 1242
<212> TYPE: DNA
<213> ORGANISM: Artificial Sequence
<220> FEATURE:
<221> NAME/KEY: P450cam C334A
<222> LOCATION: 1 1242
<223> OTHER INFORMATION: Mutant with Cys-334 (tgc at nucleotides 1000
      1002) substituted with Ala

<400> SEQUENCE: 2

```
acg act gaa acc ata caa agc aac gcc aat ctt gcc cct ctg cca ccc       48
Thr Thr Glu Thr Ile Gln Ser Asn Ala Asn Leu Ala Pro Leu Pro Pro
1               5                   10                  15 cat gtg cca gag cac ctg gta ttc gac ttc gac atg tac aat ccg tcg       96
His Val Pro Glu His Leu Val Phe Asp Phe Asp Met Tyr Asn Pro Ser
            20                  25                  30 aat ctg tct gcc ggc gtg cag gag gcc tgg gca gtt ctg caa gaa tca      144
Asn Leu Ser Ala Gly Val Gln Glu Ala Trp Ala Val Leu Gln Glu Ser
        35                  40                  45 aac gta ccg gat ctg gtg tgg act cgc tgc aac ggc gga cac tgg atc      192
Asn Val Pro Asp Leu Val Trp Thr Arg Cys Asn Gly Gly His Trp Ile
    50                  55                  60 gcc act cgc ggc caa ctg atc cgt gag gcc tat gaa gat tac cgc cac      240
Ala Thr Arg Gly Gln Leu Ile Arg Glu Ala Tyr Glu Asp Tyr Arg His
65                  70                  75                  80 ttt tcc agc gag tgc ccg ttc atc cct cgt gaa gcc ggc gaa gcc tac      288
Phe Ser Ser Glu Cys Pro Phe Ile Pro Arg Glu Ala Gly Glu Ala Tyr
                85                  90                  95 gac ttc att ccc acc tcg atg gat ccg ccc gag cag cgc cag ttt cgt      336
Asp Phe Ile Pro Thr Ser Met Asp Pro Pro Glu Gln Arg Gln Phe Arg
```

-continued

```
                100                   105                   110
gcg ctg gcc aac caa gtg gtt ggc atg ccg gtg gtg gat aag ctg gag        384
Ala Leu Ala Asn Gln Val Val Gly Met Pro Val Val Asp Lys Leu Glu
            115                   120                   125 aac cgg atc cag gag ctg gcc tgc tcg ctg atc gag agc ctg cgc ccg        432
Asn Arg Ile Gln Glu Leu Ala Cys Ser Leu Ile Glu Ser Leu Arg Pro
    130                   135                   140 caa gga cag tgc aac ttc acc gag gac tac gcc gaa ccc ttc ccg ata        480
Gln Gly Gln Cys Asn Phe Thr Glu Asp Tyr Ala Glu Pro Phe Pro Ile
145                   150                   155                   160 cgc atc ttc atg ctg ctc gca ggt cta ccg gaa gaa gat atc ccg cac        528
Arg Ile Phe Met Leu Leu Ala Gly Leu Pro Glu Glu Asp Ile Pro His
                165                   170                   175 ttg aaa tac cta acg gat cag atg acc cgt ccg gat ggc agc atg acc        576
Leu Lys Tyr Leu Thr Asp Gln Met Thr Arg Pro Asp Gly Ser Met Thr
            180                   185                   190 ttc gca gag gcc aag gag gcg ctc tac gac tat ctg ata ccg atc atc        624
Phe Ala Glu Ala Lys Glu Ala Leu Tyr Asp Tyr Leu Ile Pro Ile Ile
        195                   200                   205 gag caa cgc agg cag aag ccg gga acc gac gct atc agc atc gtt gcc        672
Glu Gln Arg Arg Gln Lys Pro Gly Thr Asp Ala Ile Ser Ile Val Ala
    210                   215                   220 aac ggc cag gtc aat ggg cga ccg atc acc agt gac gaa gcc aag agg        720
Asn Gly Gln Val Asn Gly Arg Pro Ile Thr Ser Asp Glu Ala Lys Arg
225                   230                   235                   240 atg tgt ggc ctg tta ctg gtc ggc ggc ctg gat acg gtg gtc aat ttc        768
Met Cys Gly Leu Leu Leu Val Gly Gly Leu Asp Thr Val Val Asn Phe
                245                   250                   255 ctc agc ttc agc atg gag ttc ctg gcc aaa agc ccg gag cat cgc cag        816
Leu Ser Phe Ser Met Glu Phe Leu Ala Lys Ser Pro Glu His Arg Gln
            260                   265                   270 gag ctg atc gag cgt ccc gag cgt att cca gcc gct tgc gag gaa cta        864
Glu Leu Ile Glu Arg Pro Glu Arg Ile Pro Ala Ala Cys Glu Glu Leu
        275                   280                   285 ctc cgg cgc ttc tcg ctg gtt gcc gat ggc cgc atc ctc acc tcc gat        912
Leu Arg Arg Phe Ser Leu Val Ala Asp Gly Arg Ile Leu Thr Ser Asp
    290                   295                   300 tac gag ttt cat ggc gtg caa ctg aag aaa ggt gac cag atc ctg cta        960
Tyr Glu Phe His Gly Val Gln Leu Lys Lys Gly Asp Gln Ile Leu Leu
305                   310                   315                   320 ccg cag atg ctg tct ggc ctg gat gag cgc gaa aac gcc gcc ccg atg       1008
Pro Gln Met Leu Ser Gly Leu Asp Glu Arg Glu Asn Ala Ala Pro Met
                325                   330                   335 cac gtc gac ttc agt cgc caa aag gtt tca cac acc acc ttt ggc cac       1056
His Val Asp Phe Ser Arg Glu Lys Val Ser His Thr Thr Phe Gly His
            340                   345                   350 ggc agc cat ctg tgc ctt ggc cag cac ctg gcc cgc cgg gaa atc atc       1104
Gly Ser His Leu Cys Leu Gly Gln His Leu Ala Arg Arg Glu Ile Ile
        355                   360                   365 gtc acc ctc aag gaa tgg ctg acc agg att cct gac ttc tcc att gcc       1152
Val Thr Leu Lys Glu Trp Leu Thr Arg Ile Pro Asp Phe Ser Ile Ala
    370                   375                   380 ccg ggt gcc cag att cag cac aag agc ggc atc gtc agc ggc gtg cag       1200
Pro Gly Ala Gln Ile Gln His Lys Ser Gly Ile Val Ser Gly Val Gln
385                   390                   395                   400 gca ctc cct ctg gtc tgg gat ccg gcg act acc aaa gcg gta              1242
Ala Leu Pro Leu Val Trp Asp Pro Ala Thr Thr Lys Ala Val
                405                   410                   414
```